US009445870B2

(12) United States Patent
Chuck et al.

(10) Patent No.: US 9,445,870 B2
(45) Date of Patent: Sep. 20, 2016

(54) METHODS AND DEVICES FOR CROSSLINKING OF CORNEAL COLLAGEN AND FOR TREATMENT OF DISORDERS OF THE EYE

(75) Inventors: Roy S. Chuck, Great Neck, NY (US); Barbara Ann Soltz, Spring Valley, NY (US); Robert Soltz, Spring Valley, NY (US)

(73) Assignees: Montefiore Medical Center, Bronx, NY (US); Conversion Energy Enterprises Inc., Spring Valley, NY (US)

( * ) Notice: Subject to any disclaimer, the term of this patent is extended or adjusted under 35 U.S.C. 154(b) by 723 days.

(21) Appl. No.: 13/576,589

(22) PCT Filed: Feb. 1, 2011

(86) PCT No.: PCT/US2011/023401
§ 371 (c)(1),
(2), (4) Date: Apr. 18, 2013

(87) PCT Pub. No.: WO2011/094758
PCT Pub. Date: Aug. 4, 2011

(65) Prior Publication Data
US 2013/0211389 A1    Aug. 15, 2013

Related U.S. Application Data

(60) Provisional application No. 61/337,271, filed on Feb. 1, 2010.

(51) Int. Cl.
*A61F 9/007* (2006.01)
*A61N 5/06* (2006.01)
(Continued)

(52) U.S. Cl.
CPC ............. *A61B 18/20* (2013.01); *A61F 9/0079* (2013.01); *A61N 5/062* (2013.01); *A61F 2009/00872* (2013.01)

(58) Field of Classification Search
CPC ................... A61F 9/0079; A61F 2009/00872; A61B 18/20; A61N 5/062
USPC .......................................... 606/4–6; 128/898
See application file for complete search history.

(56) References Cited

U.S. PATENT DOCUMENTS 4,014,321 A * 3/1977 March ........................... 600/319
5,618,284 A    4/1997 Sand
(Continued)

OTHER PUBLICATIONS

PCT International Search Report and Written Opinion, dated Jul. 13, 2012 in connection with PCT International Application No. PCT/US2011/23401, 12 pages.
(Continued)

*Primary Examiner* — Lynsey Crandall
*Assistant Examiner* — Nathan J Jenness
(74) *Attorney, Agent, or Firm* — Amster, Rothstein & Ebenstein LLP

(57) ABSTRACT

Methods and devices for delivering therapeutic or diagnostic energy (e.g., light, ultrasound, ionizing radiation (e.g., x-ray), vibration, heat energy, etc.) into the eye. An energy emitting device is positioned on the eye and used to deliver energy into the eye. The device may be constructed to allow the subject's eyelids to open and close while the device is positioned on the eye. The device is useable for various energy based or energy-mediated therapies, including crosslinking of corneal collagen, light therapy, photodynamic therapy, photo-activation of drugs, etc.

15 Claims, 5 Drawing Sheets

(51) Int. Cl.
*A61B 18/20* (2006.01)
*A61F 9/008* (2006.01)

(56) References Cited

U.S. PATENT DOCUMENTS

| | | |
|---|---|---|
| 2006/0231107 A1 | 10/2006 | Glickman et al. |
| 2008/0208177 A1 | 8/2008 | Mrochen et al. |
| 2009/0149842 A1 | 6/2009 | Muller et al. |
| 2009/0171305 A1* | 7/2009 | El Hage .................. 604/294 |
| 2009/0189974 A1 | 7/2009 | Deering |
| 2010/0001926 A1 | 1/2010 | Amirparviz et al. |
| 2012/0041520 A1* | 2/2012 | Colbaugh ............ A61N 5/0618 607/88 |

OTHER PUBLICATIONS

PCT International Preliminary Report on Patentability and Written Opinion of the International Searching Authority dated Jul. 13, 2012 in connection with PCT International Patent Application No. PCT/US2011/23401, 10 pages.

* cited by examiner

METHODS AND DEVICES FOR CROSSLINKING OF CORNEAL COLLAGEN AND FOR TREATMENT OF DISORDERS OF THE EYE

RELATED APPLICATION

This application is a 35 U.S.C. §371 national stage of PCT International Patent Application No. PCT/US2011/23401 entitled Methods and Devices for Crosslinking of Corneal Collagen and for Treatment of Disorders of the Eye filed Feb. 1, 2010, which claims priority to U.S. Provisional Patent Application No. 61/337,271 entitled Photochemical Stabilization Of Orlhokeratology-Induced Refractive Error Correction Of Corneal Tissues Using A Light 5 Emitting Contact Lens filed Feb. 1, 2010, the entire disclosures of which are expressly incorporated herein by reference.

FIELD OF THE INVENTION

The present invention relates generally to the fields of biology, medicine, optics and electronics and more particularly to methods and devices for delivering energy (e.g., light, ultrasound, ionizing radiation (e.g., x-ray), vibration, heat energy, etc.) into the eye alone or in combination with chemical agent(s) to cause desired therapeutic or diagnostic effects.

BACKGROUND OF THE INVENTION

Pursuant to 37 CFR 1.71(e), this patent document contains material which is subject to copyright protection. The copyright owner has no objection to facsimile reproduction of the entire patent document or the patent disclosure, as it appears in the Patent and Trademark Office patent file or records, but otherwise reserves all copyright rights whatsoever.

The anterior aspect of a human eye generally includes a clear, dome-shaped cornea that covers the anterior chamber and iris. Light passes through the cornea, through the clear fluid that fills the anterior chamber, through an opening in the iris and then through the eye's lens. The cornea is devoid of blood vessels, except at its margins, but it does contain many nerves. The cornea receives nutrients and oxygen from tears which bathe its anterior surface and aqueous humour which contacts the posterior side of the cornea.

The cornea helps to focus light as it enters the eye. The curvature of the cornea provides its focusing power. Light entering the eye is partially refracted by the cornea before reaching the lens. Also, the cornea serves as a protective cover to prevent foreign matter from injuring the pupil, the iris or the inside of the eye.

The cornea has an outer (anterior) epithelial layer, an inner (posterior) endothelium and a relatively thick stroma positioned between the epithelial layer and endothelium. A thin, smooth membrane, known as Bowman's Layer, lies between the epithelial layer and the anterior surface of the stroma. Another thin membrane, known as Descemet's Layer, lies between the posterior surface of the stroma and the endothelium. The stroma, as well as Bowman's Layer, contains strong collagen fibers which define the shape of the cornea. The collagen fibers within the stroma are arranged in a regular, geometric fashion which provides the needed transparency.

A number of pathological disorders may cause the shape of the cornea to change adversely. Generally, Corneal Ectasia is caused by biomechanical weakening or destabilization of the cornea. Corneal Ectasia sometimes occurs as a complication of refractive surgery such as LASIK. In one type of Corneal Ectasia, known as Keratoconus, the cornea thins and becomes abnormally conical in shape. Keratoconus is relatively common, affecting about one person in a thousand. At present, Keratoconus and Corneal Ectasias resulting from refractive surgery are common indications for corneal transplantation. However, corneal transplantation is expensive, requires substantial recovery time, can utilize scarce donor tissues and has inherent risks of post-surgical complications. Thus, any treatment that can delay or prevent the need for corneal transplantation in these patients may be of substantial benefit.

Orthokeratology is a process that uses specially designed rigid contact lenses to temporarily reshape the contour of the cornea to correct refractive errors resulting from routine disorders such myopia or other pathologies such as Corneal Ectasia or Keratoconus. Normally, the corrective orthokeratology lenses are worn only at night. In some cases, a series of orthokeratology lenses having progressively greater curvature are used over a period of days or weeks to achieve the needed degree of corneal reshaping. After the desired reshaping of the cornea has been attained, the cornea tends to revert back to its original shape unless measures are taken to maintain the orthokeratologically-corrected corneal shape.

One measure that is sometimes taken to maintain the corrected corneal shape is to periodically insert and wear a specifically shaped orthokeratology lens (e.g., a "retainer") to maintain the corrected corneal shape. Another approach that has been described is "fixing" the cornea in its corrected shape by crosslinking of corneal collagen fibers. Crosslinking of corneal collagen fibers without orthokeratology has also been used and reported as a means for deterring progression of corneal disorders such as Corneal Ectasia or Keratoconus. Generally, crosslinking of corneal collagen has heretofore been effected by administering ultraviolet A light (UVA) combined with riboflavin (Vitamin B2). Typically, in this procedure, anesthesia drops are administered to the eye and the epithelial layer is removed. Riboflavin drops are then administered. The riboflavin acts both to enhance the crosslinking effect of the UVA and, also, to absorb a substantial amount of the UVA thereby preventing it from damaging the retina or other deeper structures of the eye. After the riboflavin has been administered, the patient must look into an extracorporeally-positioned ultraviolet light for a period of time (e.g. 30 minutes). At the conclusion of this procedure, a corneal bandage in the nature of a soft contact lens is applied to the anterior surface of the cornea from which the epithelium has been removed. This corneal bandage is typically left in place for a number of days and must then be removed. Antibiotic and anti-inflammatory drops are typically used for about two weeks after the procedure.

Also, U.S. Patent Publication No. 2001/016,731 (Devore et al.) describes an orthokeratology method that includes the steps of softening of the cornea with a softening agent, applying a mold (e.g., a shaping contact lens) to reshape the cornea to a desired anterior curvature, and rapidly restabilizing or "fixing" the corneal tissues so that the cornea retains its new configuration. A chemical softening agent, such as glutaric anhydride is applied to the cornea to soften the cornea, after which a specially designed mold of predetermined curvature and configuration is applied to the cornea. Slight downward pressure is applied to the mold for a predetermined period of time to re-shape the cornea. The mold is maintained in position while a stabilizing agent, such as a UV light source, is positioned above the mold (i.e.

not in direct contact with the patient's eye. The UV light, is applied to the cornea for a predetermined time to "restabilize" the corneal tissue so that the cornea retains its shape upon removal of the mold. The stabilization process can also be used for patients having already undergone traditional orthokeratology to eliminate the need to continue wearing a retainer to maintain the shape of the cornea.

There remains a need in the art for the development of new devices and methods for crosslinking corneal collagen in ways that are safer, easier and potentially less costly.

SUMMARY OF THE INVENTIONS

The present invention provides methods and devices for delivering therapeutic or diagnostic energy to the eye of a human or animal subject, wherein an energy-emitting device is placed on the subject's eye and is then used to deliver therapeutic or diagnostic energy (e.g., light, ultrasound, ionizing radiation (e.g., x-ray), vibration, heat energy, etc.) into the eye. In some embodiments, the device may be constructed to allow the subject's eye lids to open and close while the energy-emitting device is positioned on the eye. In some embodiments, the energy emitting device may comprise a self contained energy emitting contact lens device having a contact lens body, a power source and one or more energy emitters positioned on or in the contact lens body. In other embodiments, the device may include an energy-emitting contact lens device in combination with a separate apparatus, such as a power and/or control module, that remains outside of the subject's eye and is connected to the energy emitting contact lens device by wireless or wired connection.

Further in accordance with the present invention, there are provided methods and devices for crosslinking corneal collagen using a light-emitting contact lens device of the foregoing character that is placed on the anterior surface of the cornea generally in the manner of a regular contact lens. In some embodiments, the light-emitting contact lens may be shaped to exert desired force on the cornea concurrently with the delivery of crosslinking light radiation (e.g., UVA with or without accompanying administration of an ancillary agent such as riboflavin), thereby effecting or maintaining a desired cornea shape as the collagen crosslinking takes place. Because the light-emitting contact lens device is worn on the eye, the patient is not required to look into an extracorporeally-positioned light-emitting source and may remain ambulatory and/or outside of a physician's office or medical facility during the treatment. Also, in at least some embodiments of this invention, need for removal of the epithelial layer may be minimized or avoided in its entirety, thereby also eliminating any need for application and later removal of a corneal bandage.

In accordance with one aspect of the invention, there is provided a light-emitting contact lens device that comprises a contact lens body, a power source and at least one light emitter for emitting collagen-crosslinking light into a cornea on which the device is positioned.

Further in accordance with the invention, there is provided a method for crosslinking corneal collagen in the eye of a human or animal subject comprising the steps of: a) placing on the subject's eye a light-emitting device that allows the subjects eye lids to open and close while the light-emitting device is positioned on the eye and b) causing the light-emitting device to emit a collagen-crosslinking light into the cornea of the eye, thereby crosslinking collagen within that cornea. A photo-absorbing and/or photo-protective agent, such as riboflavin, or other agent that facilitates the desired crosslinking of collagen, may be administered prior to or concurrently with emission of the collagen-crosslinking light. Optionally, before placing the light-emitting device on the eye, some or all of the epithelial layer may be removed or disrupted (physically or chemically) by known techniques. However, in some embodiments, the residence of the light-emitting device on the anterior surface of the cornea will cause the epithelial layer to become sufficiently permeable to allow an effective amount of a photo-absorbing and/or photo-protective agent, such as riboflavin, to enter the cornea without the need for prior removal or disruption of the epithelial layer. In this regard, the eye-contacting inner surface of the device may be configured to cause a desired disruption or increased permeability of the epithelial layer and/or may be coated or loaded with a photo-absorbing and/or photo-protective agent, such as riboflavin, such that the agent elutes or applies directly from the device into the underlying corneal tissue.

Still further in accordance with the present invention, the light-emitting devices and methods described herein may be used with or without orthokeratological reshaping of the cornea. For example, in cases where it is simply desired to maintain the present shape of the cornea (e.g., to halt or slow early-stage progression of a disease like Corneal Ectasia or Keraconus) a light-emitting device of the present invention may be used to effect crosslinking of corneal collagen without prior or concurrent orthokeratological reshaping of the cornea. In other cases, such as those where it is desired to correct a refractive disorder of the eye, orthokeratological reshaping of the cornea may be effected prior to and/or concurrently with the use of a light-emitting device of the present invention to effect crosslinking of corneal collagen. In this regard, some embodiments of the light-emitting devices of the present invention may be specifically shaped to exert desired force(s) on the cornea to cause or maintain a therapeutically modified shape of the cornea during the collagen crosslinking process.

Still further in accordance with the present invention, the light-emitting devices of the present invention may be used to deliver light energy that is, in itself, therapeutic (e.g., antimicrobial-antibiotic, antiviral, antiparacytic, antifungal, microbicidal, bactericidal, fungicidal, sporicidal, disinfectant, etc.) and/or to effect a photo-activated therapy in combination with an administered agent, such as in photo-dynamic therapy or photosensitization. In general, photosensitization is a treatment wherein a photoactive compound is administered and selectively accumulates in target cells. Thereafter, light energy (e.g., visible light) is administered to the target cells. The interaction of the photoactive compound with the light, in the presence of oxygen, results in a number of cytotoxic reactions that locally destroy target microorganisms. Photosensitization can be a potential alternative to the use of antimicrobial drugs. Examples of photosensitizers that may be used for this purpose include compounds that have a tetrapyrrole nucleus, such as porphyrins, chlorines, bacteriochlorins, phthalocyanines and texaphyrins. Further examples of photosensitizers and relevant dosages and methods of use are described in Hamblin, M. R., et al. *Photodynamic therapy: a new antimicrobial approach to infectious disease?*; Photochem. Photobiol. Sci., 2, 436-450 (2004) and Joni, G., *Photodynamic Therapy of Microbial Infections: State of the Art and Perspectives*; Journal of Environmental Pathology, Toxicology, and Oncology, 25(1-2)505-519 (2006). As explained above in connection with the use of collagen crosslinking agents, in some cases where a light emitting device of the present invention is used in combination with a photosensitizer or other agent to effect photodynamic therapy (e.g., photosensitization), some or all of the epithelial layer may be removed or disrupted (physically or chemically) by known techniques to facilitate distribution of the photosensitizer. In some of these instances, the residence of the light-emitting device on the anterior surface of the cornea will cause the epithelial layer to become sufficiently permeable to allow an effective amount of the photosensitizer or other photodynamic therapy agent to enter the cornea without the need for prior removal or disruption of the epithelial layer. In this regard, the eye-contacting inner surface of the device may be configured to cause a desired disruption or increased permeability of the epithelial layer and/or may be coated or loaded with the photosensitizer or other photodynamic therapy agent such that the photosensitizer or other photodynamic therapy agent will elute or be delivered from device into the underlying corneal tissue.

Still further in accordance with the present invention, there are provided methods and systems wherein an energy-emitting contact lens device of the present invention is positioned on the eye of a subject and used to deliver energy for diagnostic purposes, and various sensing apparatus are then used to image or sense variable(s) resulting from the energy emitted into the eye (e.g., measuring back-scattered light, stimulated autofluorescence, incorporated exogenous dye fluorescence) for imaging and other diagnostic applications at the ocular surface and deeper in the eye.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

DETAILED DESCRIPTION OF THE INVENTION

The following detailed description and the accompanying drawings to which it refers are intended to describe so e, but not necessarily all, examples or embodiments of the invention. The described embodiments are to be considered in all respects only as illustrative and not restrictive. The contents of this detailed description and the accompanying drawings do not limit the scope of the invention in any way.

Figure 1:
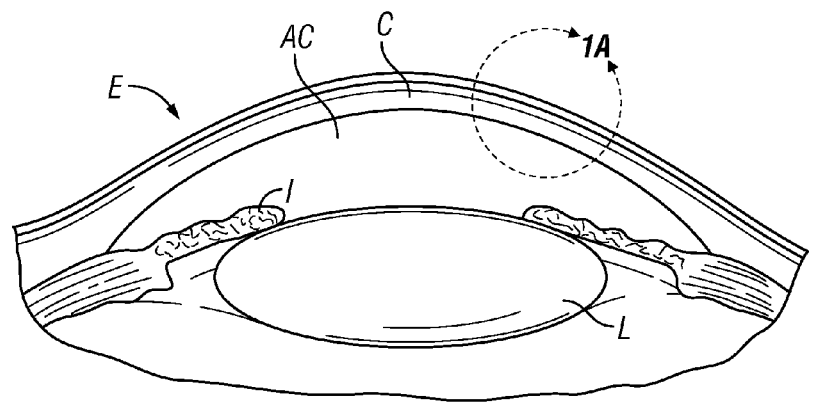
FIG. 1 is a coronal sectional view of an anterior portion of a human eye.

As shown in FIG. 1, the anterior aspect of a human eye E generally includes the cornea C, anterior chamber AC, iris I and lens L. The clear, dome-shaped cornea C covers the iris I.

Figure 1A:
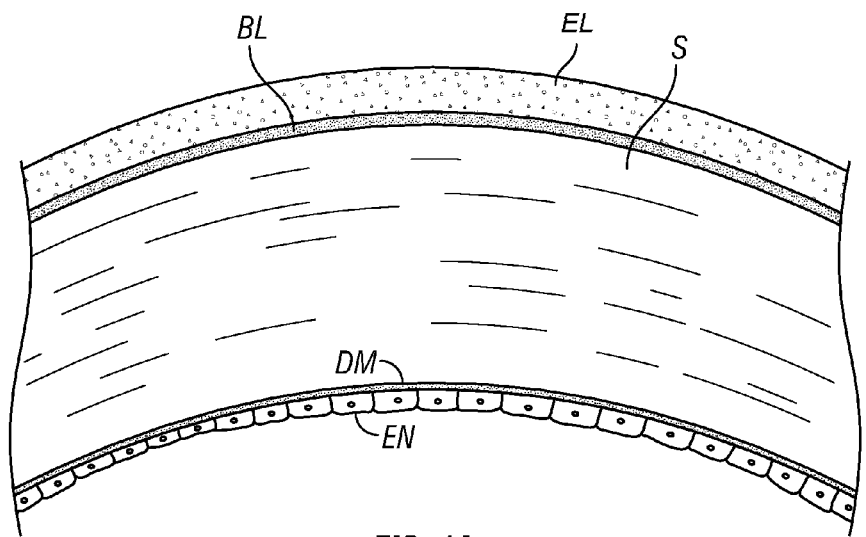
FIG. 1A is an enlarged view of region 1A of FIG. 1, showing the various histological layers of the eye's cornea.

The various layers of the cornea C are shown in the cross-sectional view of FIG. 1A. As shown, the cornea C has an outer (anterior) epithelial layer EL, an inner (posterior) endothelium EN and a relatively thick stroma S between the epithelial layer EL and endothelium EN. The membranous Bowman's Layer BL, lies between the epithelial layer EL and stroma S. Descemet's Layer DL is a thin basement membrane that lies between the stroma S and endothelium EN. Collagen fibers present in the stroma S and in Bowman's Layer BL essentially define the shape of the cornea C. The collagen fibers within the stroma S are arranged in a regular, geometric fashion which provides the needed transparency. The endothelium EN and Descemet's Layer DL play a roll in regulating the fluid content of the cornea C. If endothelial cells are lost due to trauma or disease, other existing endothelial cells will enlarge or expand to fill the unoccupied space, but no new endothelial cells will be produced. If too many endothelial cells are ultimately lost, the endothelial layer's fluid regulating function may be impaired, giving rise to edema or excess fluid within the cornea and resultant visual impairment, surface changes and pain.

Figure 2A:
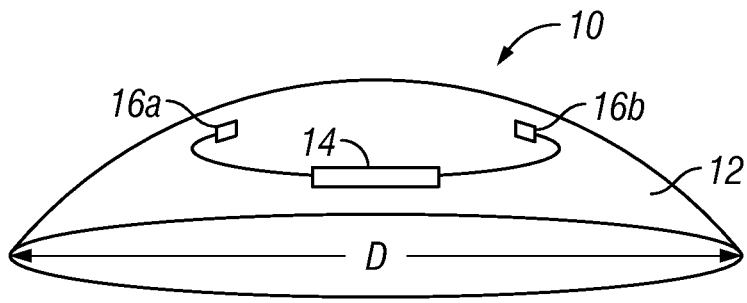
FIG. 2A is a side perspective view of one embodiment of an energy-emitting contact lens device of the present invention.
Figure 2B:
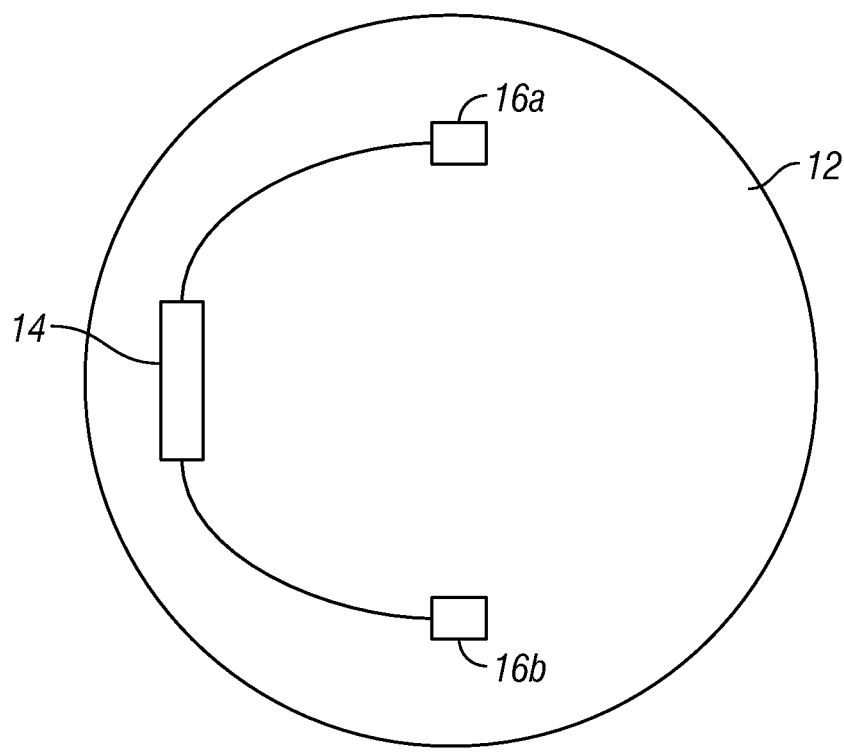
FIG. 2B is a top view of the device of FIG. 2A.

FIGS. 2A and 2B show a relatively basic embodiment of a light-emitting contact lens device 10 of the present invention. This device 10 comprises a concave lens body 12 having an open bottom of diameter D. Positioned on or in the lens body 12 is one or more power supply 14 and one or more light emitters 16a and 16b. The light emitters 16a, 16b are connected to and receive power from the power supply 14. The light emitters 16a, 16b, when energized, emit light toward the underside of the lens body 12 so that the emitted light enters the cornea C of an eye E on which this device 10 is positioned. In the particular example shown in FIGS. 2A and 2B, there are two (2) light emitters. It is to be appreciated, however, that a single light emitter or any other plurality of light emitters may be used.

Figure 3A:
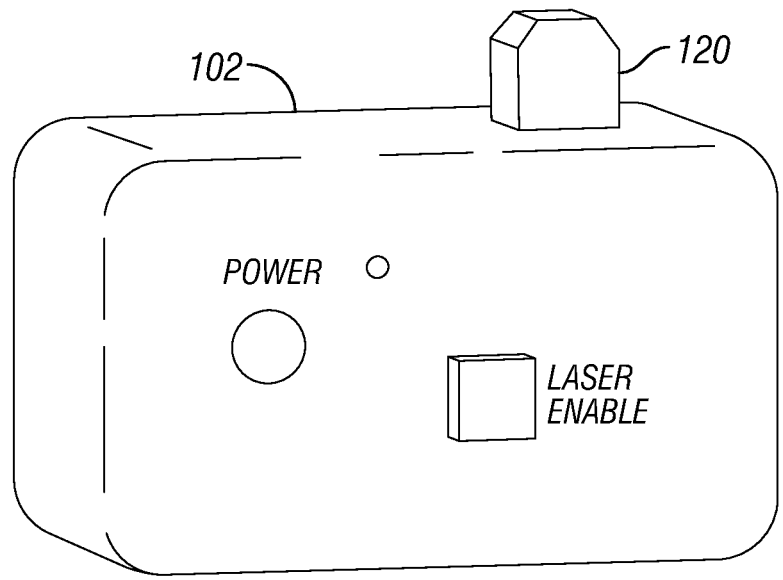
FIG. 3 is a schematic showing of a system of the present invention comprising another embodiment of an energy-emitting contact lens device in combination with a power source that is connected to circuitry on the contact lens device by wireless connection.
Figure 3B:
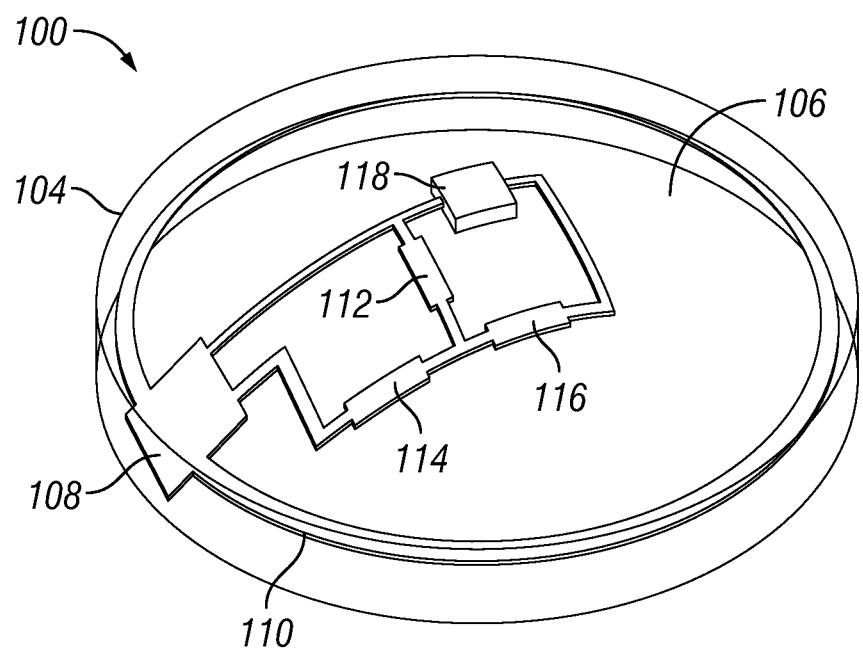
Figure 4A:
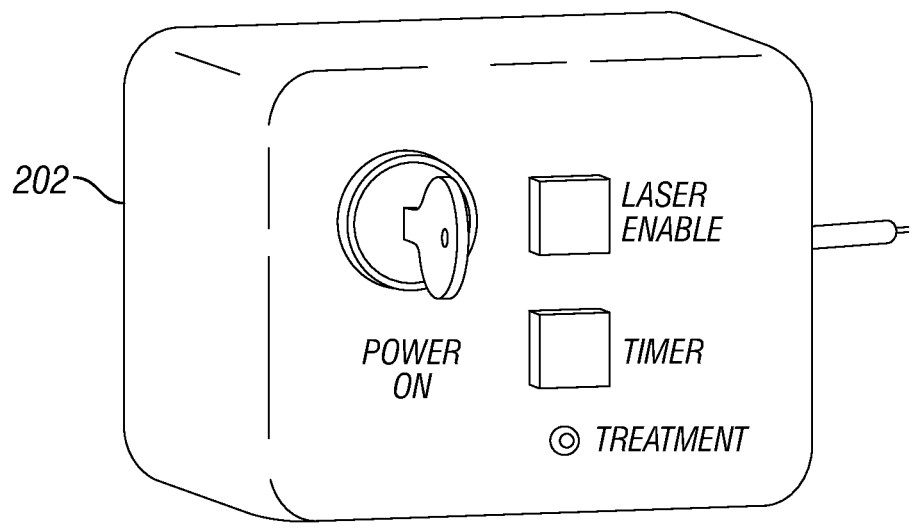
FIG. 4 is a schematic showing of a system of the present invention comprising another embodiment of an energy-emitting contact lens device in combination with a power source that is connected to circuitry on the contact lens device by a hard-wired connection.
Figure 4B:
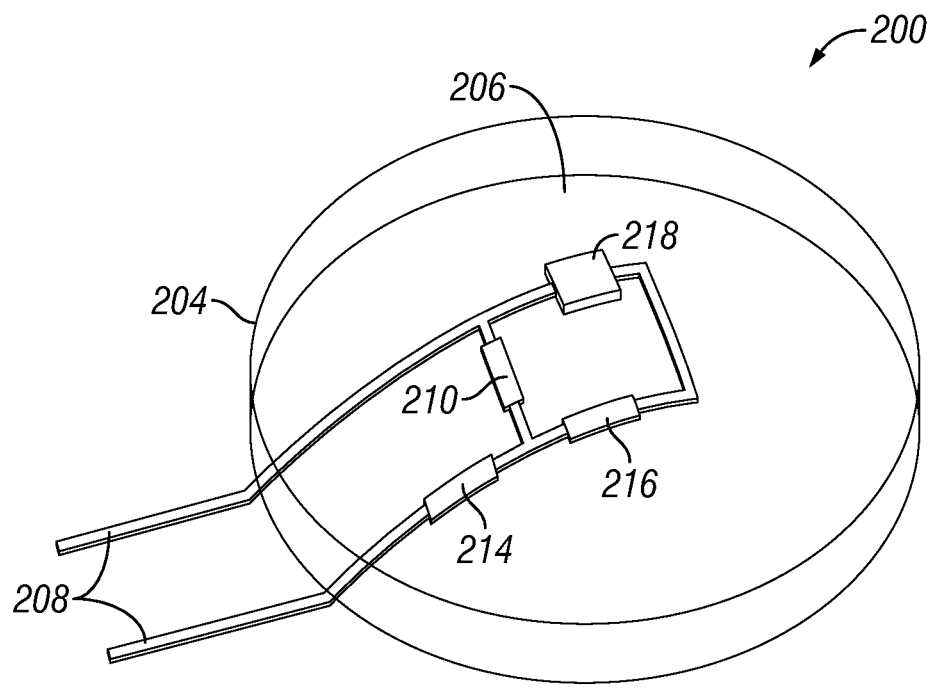

The particular number, type, size and positioning of the power source 14 may be selected based on the intended application and use of the device 10. For example, the power source 14 may comprise any battery of suitable size, longevity and power output to power the light source(s) 16a, 16b for the intended period of time, such as a thin film battery (e.g., a "microbattery") or small button type battery. Examples of thin film batteries that may be useable in at least some embodiments of the present invention include, but are not necessarily limited to, those described in U.S. Pat. Nos. 7,144,655 (Jenson, et al.) entitled Thin-Film Battery Having Ultra-Thin Electrolyte; 7,052,801 (Park et al.) entitled Anode Thin Film For Lithium Secondary Battery And Preparation Method Thereof and U.S. Patent Application Publication No. 2009/0010462 (Ekchian et al.) entitled Compact Rechargeable Thin Film Battery System For Hearing Aid, the entire disclosure of each such patent and published patent application being expressly incorporated herein by reference. Alternatively, the power source may comprise external batteries, other microbatteries, solar circuits, external radiofrequency devices connected via thin wire, magnetic capacitors, chemicals that generate power via exothermal chemical reaction and kinetic systems (such as those used in self-winding wristwatches). In alternative embodiments where all or part of the power source is located apart from the contact lens body 12, the power source may be connected to the circuitry on or in the contact lens body 12 by any suitable wired or wireless means, specific examples of which are shown in FIGS. 3 and 4 and described below. Another example of such an alternative power source is described in U.S. Patent Application Publication No. 2010/0001926 (Amirparviz et al.) entitled Contact Lens with Integrated Light Emitting Component, which describes a contact lens system wherein light shines from a contact lens to a location outside the subject's body, the entire disclosure of which is expressly incorporated herein by reference.

Also, the particular number, type, size and positioning of the one or more light emitter(s) 16a, 16b may be selected based on the intended application and use of the device 10. For example, in embodiments of the device intended for use in crosslinking corneal collagen, the light emitter(s) may comprise one or more light emitting diodes (LEDs), micro LEDs, laser diodes, light emitting chips, light emitting semiconductors, microchip lasers, etc. In embodiments where collagen crosslinking is being performed with riboflavin, the light emitter will preferably emit ultraviolet A or blue light. In some embodiments, the light emitter(s) 16a, 16b may emit light at about 360 to about 370 nanometers, preferably about 365 nm, with an intensity of about 3 mW/cm$^2$ for at least about 30 minutes, but such time period may be longer or shorter, as needed. Alternatively or more specifically, to crosslink collagen in conjunction with riboflavin, the one or more light emitter(s) 16a, 16b may emit ultraviolet A light at about 5.4 mJ/cm with corresponding irradiance is about 3 mW/cm2. Alternatively or more specifically, the one or more light emitter(s) may comprise one ore more small light emitters, such as light emitting diodes (LEDs), micro LEDs, light emitting chips, light emitting semiconductors, microchip lasers, other emitters of UVA or blue light, or emitters of any collagen crosslinking light, from the device 10 into the cornea C.

Examples of micro LEDs are described in U.S. Pat. No. 6,410,940, the entire disclosure of which is expressly incorporated by reference. Arrays of these micro LEDs require only low DC voltage (several volts) with a typical current level of tens of mA. An individual micro-LED is typically hundreds times smaller than a standard LED, thus singular micro LEDS or arrays of micro LEDs may be placed at strategic locations in or on the lens body 12 to optimize the distribution of light into the cornea C. Examples further include blue micro LEDs being developed by the University of Kansas and may incorporate or be manufactured by technologies described in United States Patent Application Publications No. 2006/0138443 (Fan et al.) entitled Encapsulation And Packaging Of Ultraviolet And Deep-Ultraviolet Light Emitting Diodes and 2006/0169993 (Fan et al.) entitled Micro-LED Based High Voltage AC/DC Indicator Lamp, the entire disclosures of which are expressly incorporated herein by reference.

The circuitry of the device 10 will incorporate a suitable switch apparatus to enable a user to energize the light emitter(s) 16a, 16b at the time of use. One type of switch apparatus that may incorporated into device 10 for this purpose is a thin strip of insulating material (e.g., a strip of semi-rigid plastic) that is initially inserted between contact points in the device's circuit, thereby holding the contact points apart and insulating the power source(s) 14 from the light emitter(s) 16a, 16b until such time as the strip is it is removed (e.g., pulled out). In this manner, the user may power up the device 10 immediately prior to use by simply pulling out the insulating strip.

In this example, the power source(s) 14, light emitter(s) 16a, 16b and associated circuitry (e.g., thin wires or strips of electrically-transmissive material connecting the power source(s) 14 to the light emitter(s) 16a, 16b as well as the on-off switching apparatus) may be mounted on or in a contact lens body 12 in any suitable manner. In some embodiments, such as those where it is desired for the device 10 to exert a shape-modifying or shape-retaining force on the cornea C, the contact lens body 12 may be formed of rigid or gas permeable rigid material of a type known or suitable for contact lens construction. Examples of such materials include polymethyl methacrylates. In other embodiments, such as those where the device 10 is being used to cast light into the cornea C to effect light-based antimicrobial (e.g., antibiotic, antiviral, antiparacytic, antifungal, microbicidal, bactericidal, fungicidal, sporicidal, disinfectant, etc.) effects, collagen crosslinking, photosensitization or photodynamic therapy without exerting a shape-modifying or shape-retaining force on the cornea C, the contact lens body 12 may be formed of a soft material of a type known or suitable for soft contact lens construction. Examples of such materials include hydrogels and silicone hydrogels.

Because it is desired for the subject's eye lids to open and close over the device 10 while the device 10 is positioned on the eye, it is generally desirable for the anterior and posterior surfaces of the device 10 to be relatively smooth. One way of accomplishing this will be to initially form the contact lens body 12 in two pieces—i.e., an anterior or top portion and a posterior or bottom portion. The power source(s) 14, light emitter(s) 16a, 16b and associated circuitry (e.g., thin wires or strips of electrically-transmissive material connecting the power source(s) 14 to the light emitter(s) 16a, 16b as well as the on-off switching apparatus) may then be placed in their appropriate positions between the top portion and bottom portion of the lens body 12 and those portions may then be fused together, thereby forming a unitary lens body 12 in which the power source(s) 14, light emitter(s) 16a, 16b and associated circuitry (e.g., thin wires or strips of electrically-transmissive material connecting the power source(s) 14 to the light emitter(s) 16a, 16b as well as the on-off switching apparatus) are captured between the fused upper and lower portions. Any removable insulator strip to be used as an on/off switch may be allowed to protrude from one edge of the fused contact lens body, so that it may easily be removed to energize the device when desired.

Alternative materials, means, components and an imbedded/etched circuit mold for constructing the device 10 are also described in U.S. Patent Application Publication No. 2010/0001926 (Amirparviz et al.) entitled Contact Lens with Integrated Light Emitting Component, which describes a contact lens system wherein light shines from a contact lens to a location outside the subject's body, the entire disclosure of which is expressly incorporated herein by reference. The device 10 could be also, alternatively, be constructed by mounting the components 14, 16a, 16b on top of a contact lens body, especially is the components are sufficiently flat or of low enough profile to allow the eye lids to open and close over the device.

FIGS. 3 and 4 show alternative embodiments of energy emitting contact lens devices of the present invention in combination with a component (e.g., a power source and/or controller) that resides outside of the subject's eye and communicate with the circuitry on or in the contact lens by wireless or hard wired connection.

Specifically, FIG. 3 shows an embodiment of a wireless system 100 that comprises a radiofrequency controller 102 in combination with an energy emitting contact lens device 104. In this example, the energy emitting contact lens device 104 comprises a contact lens body 106 as described above. Positioned on or in the contact lens body 106 is circuitry, such as a laser cut or etched circuit comprising a power module, 108, antenna 110, Zener diode 112, resisters 114, 116 and a laser diode 106 which emits the desired energy downwardly through the undersurface of the contact lend body 106 and into an eye on which the contact lens device 104 is positioned. The controller 120, when energized, sends radiofrequency or other suitable energy signals from its antenna 120 to the antenna 110 of the contact lens circuitry. This causes powering up of the power module 108 which in turn results in emission of energy from the laser diode 118 into the eye.

FIG. 4 shows an embodiment of a hard wired system 200 that comprises a controller 202 having a power on/power off switch, a power on/power off indicator light, a laser enable switch, a timer and a treatment-in-progress indicator light in combination with an energy emitting contact lens device 204. In this example, the energy emitting contact lens device 204 comprises a contact lens body 206 as described above. Positioned on or in the contact lens body 206 is circuitry, such as a laser cut or etched circuit comprising a Zener diode 210, resisters 214, 216 and a laser diode 218 which emits the desired energy downwardly through the undersurface of the contact lend body 206 and into an eye on which the contact lens device 204 is positioned. Thin wires 208 extend from one side of the energy emitting contact lens device 204 and connect the circuitry on or in the contact lens body 206 to the controller 202. The controller 202 sends power via wires 208 to the circuitry on or in the contact lens body 206. This causes emission of energy from the laser diode 118 into the eye. The thin wires 208 may be small enough in diameter to extend out of one side of the eye during treatment, thereby allowing the subject's eyelids to open and close during treatment.

The circuit lay-outs and electronic components of the devices 100, 200 shown in FIGS. 3 and 4 are commercially available or may be custom made. Commercially available light emitting laser diodes may be used to deliver any desired type of light (e.g., red, white, green, blue, UV, UVA, etc.). Laser diodes that are commercially available from various sources, including Sanyo Electric Co., Ltd. Tottori City, Japan and Sony Corporation, Tokyo, Japan. In some embodiments, laser diodes having small, flat configurations may be employed for wearer comfort and, where possible, to allow the subject's eyes to open and close while wearing the device. See, for example, Heyler, Randy A., et al.; *Low-Profile Flat Pack: A High-Power Fiber Coupled Laser Diode Package for Low-Cost High-Reliability Applications*; Proc. SPIE 5358, 29 (2004).

Figure 5B:
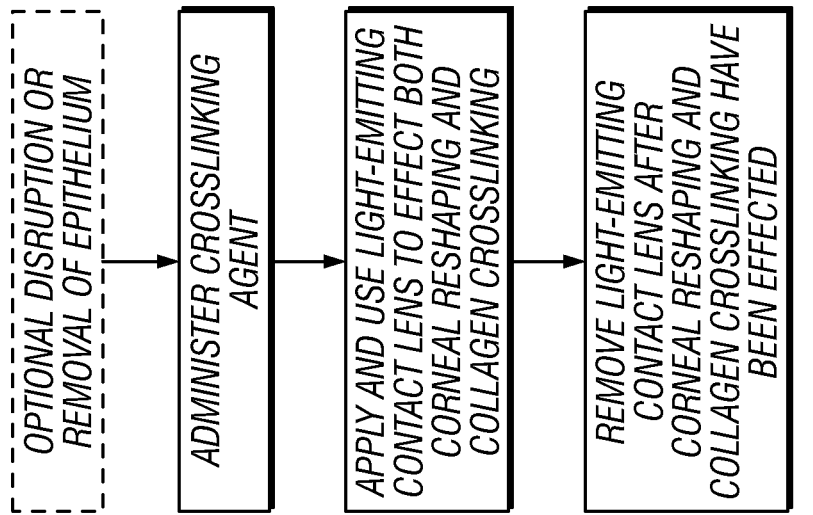
FIG. 5B is a flow diagram showing steps in another method wherein a light-emitting device of the present invention is used to effect crosslinking of corneal collagen and reshaping of the cornea without prior reshaping of the cornea by other means.
Figure 5A:
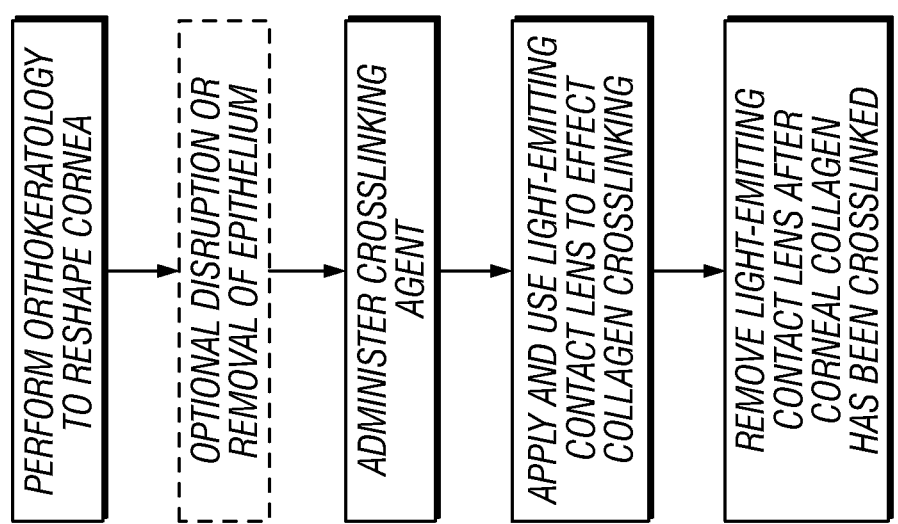
FIG. 5A is a flow diagram showing steps in one method wherein a light-emitting device of the present invention is used to effect crosslinking of corneal collagen after the cornea has been reshaped by other means, such as orthokeratology.

FIGS. 5A and 5B are flow diagrams outlining two non-limiting examples of methods whereby a light emitting contact lens device 10 of the present invention is used for crosslinking corneal collagen. In the method of FIG. 3A, the device 10 is used after the subject's cornea has been reshaped by orthokeratology (or other suitable techniques). In the method of FIG. 3B, the device 10 is used without prior reshaping of the subject's cornea has been reshaped by orthokeratology or any other cornea-reshaping technique.

In either of the methods of FIG. 5A or 5B, it may be desirable or clinically indicated to remove or disrupt the epithelial layer EL of the cornea C to facilitate subsequent distribution of effective amounts of the riboflavin or other agent into the cornea C and/or anterior chamber AC. As those of skill in the art understand, this can be achieved in various ways. For example, the epithelial layer EL may be chemically removed using an alcohol solution of about 20% concentration, it may be physically debrided by rubbing with a sponge or scraping with a scraping instrument, it may be incised or disrupted by cutting with a scalpel, or any other known technique. If the clinician elects debriding, the epithelial layer may be removed from an area typically of about 4 to 9 mm, preferably about 5-8 mm, and most preferably about 5-6 mm in diameter. Alternatively, vertical and horizontal cuts, for example, scalpel cuts, can be made in the epithelial layer. Two or more, for example, three vertical slits and one or more horizontal slit, of about 1 mm width and 4 or 5 mm length can be made on the epithelium layer to help the administered crosslinking agent such as riboflavin to diffuse throughout the cornea. Also, as described above, the device 10 itself may be designed to cause disruption of the epithelium or to form small cuts in the epithelial layer EL, thereby eliminating any need for removal or disruption of the epithelial layer EL prior to the procedure. In the procedure of FIG. 3A, any optional removal or disruption of the epithelial layer EL will typically performed after the orthokeratology stage of the procedure has been completed.

With specific reference to the procedure of FIG. 5A, orthokeratology or any other suitable cornea reshaping procedure) is performed using techniques known in the art. Typically, with standard orthokeratology, special contact lenses are work nightly over a period of weeks to effect the desired modification of the corneal shape. In an alternative to orthokeratology, known as conductive keratoplasty, heated metal probes are inserted into the cornea at selected areas in order to selectively shrink colagen and change the shape of the cornea. Like orthokeratology, the changes in corneal shape resulting from conductive keratoplasty do not last indefinitely and can regress over a period of months to years. In some orthokeratology cases, a corneal softening or destabilizing agent such as an enzyme or other compositions may be used to aid or accelerate reshaping of the cornea, examples of which are described in U.S. Pat. No. 5,626,865 (Harris et al.) entitled Enzyme-Orthokeratology and U.S. Patent Application Publication No. 2001, 0016731 (Devore et al.), the entire disclosures of which are expressly incorporated herein by reference. It is to be appreciated, however, that the present invention expressly includes, but is not limited to, methods wherein no corneal softening or destabilizing agent is used.

After the corneal reshaping and any optional removal or disruption of the epithelial layer EL have been completed in the method of FIG. 5A and after any optional removal or disruption of the epithelial layer EL in the method of FIG. 5B, a crosslinking agent, such as a photoabsorbing substance, is administered topically to the eye. Such agent may comprise a riboflavin solution. One particular topical riboflavin preparation that is suitable for use in conjunction with the light emitting devices of the present invention is described in U.S. Patent Application Publication No. 2009/0171305 (El Hage) entitled Combination Therapy For Long-Lasting CKR, the entire disclosure of which is expressly incorporated herein by reference. This solution comprises dextran and riboflavin. For example, a sterile, aqueous 0.1% riboflavin solution may be prepared by dissolving 10 mg riboflavin-5-phosphate in 10 mL of 20% dextran-T-500 solution. This solution may then be administered topically to the subject's eye E for a time sufficient for the riboflavin to reach the anterior chamber AC of the eye, for example 10-15 minutes or more. If desired, an ophthalmologist or other trained observer may confirm, by slit-lamp examination, when the riboflavin has distributed into the anterior chamber AC of the eye. In some embodiments, the crosslinking agent will not be volitionally administered in a separate step of the method, but rather will be coated or disposed in or on the light emitting device 10 of the present invention such that the crosslinking agent is delivered from the device 10 to the cornea C after the device 10 has been p[laced on the eye.

In either of the methods of FIGS. 3A and 3B, a light emitting device 10 is placed on the eye and used to deliver collagen crosslinking light to the cornea C for a period of time sufficient to effect the desired degree of crosslinking of corneal collagen. This may comprise delivering blue LED light (such as light from blue micro-LEDs) or UVA light of 360 to about 370 nanometers, preferably about 365 nm, with an intensity of about 3 mW/cm$^2$ for at least about 30 minutes, but such time period may be longer or shorter, as needed. Alternatively or more specifically, to crosslink collagen in conjunction with riboflavin, the one or more light emitter(s) 16a, 16b may emit UVA light at about 5.4 mJ/cm with corresponding irradiance of about 3 mW/cm2. Because the device 10 is self contained and constructed to allow the subject's eye to open and close over the device 10, this step of the method may at least sometimes be performed while the subject is ambulatory and/or away from a physician's office or medical facility. The contact lens body 12 may be sufficiently transparent to allow the subject to have relatively normal vision while the device 10 is being used.

In both the methods of FIGS. 3A and 3B, after the desired degree of collagen crosslinking has been achieved, the device 10 is removed from the eye and discarded.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method for delivering therapeutic energy to an eye of a human or animal subject, said method comprising the steps of:
    a) administering a crosslinking agent to the eye; and
    b) placing on the subject's eye an ultraviolet light-emitting contact lens that allows the eye lids of that eye to open and close while the ultraviolet light-emitting contact lens is positioned on the eye, and causing the ultraviolet light-emitting contact lens positioned on the eye to deliver therapeutic energy into the eye sufficient to effect crosslinking of corneal collagen.

2. The method according to claim 1 wherein the contact lens emits ultraviolet light into the cornea of the subject's eye.

3. The method according to claim 2 wherein the ultraviolet light entering the cornea causes a photo-antimicrobial effect.

4. The method according to claim 1 wherein the agent comprises riboflavin.

5. The method according to claim 1 wherein the contact lens comprises a lens body and at least one light emitter.

6. The method according to claim 1 wherein the contact lens emits ultraviolet A light.

7. The method according to claim 6 wherein the ultraviolet A light is emitted with fluence of 5.4 mJ/cm$^2$ with a corresponding irradiance of 3 mW/cm$^2$.

8. The method according to claim 6 wherein the contact lens emits light having a wavelength of 360 to 370 nanometers.

9. The method according to claim 6 wherein the contact lens emits light having a wavelength of 365 nm.

10. The method according to claim 6 wherein the contact lens emits light having an intensity of about 3 mW/cm2 for a desired period of time.

11. The method according to claim 6 wherein the light is delivered into the cornea for at least 30 minutes.

12. The method according to claim 1 wherein the contact lens comprises a light emitter of a type selected from the group consisting of: light emitting diodes (LEDs), micro light emitting diodes (micro LEDs), laser diodes, blue micro LEDs, light emitting chips, light emitting semiconductors, microchip lasers and other emitters of UVA or blue light.

13. The method according to claim 1 wherein the agent is applied topically to the cornea.

14. The method according to claim 1 wherein the agent is initially on or in the contact lens and is subsequently delivered from the contact lens into the eye.

15. The method according to claim 1 further comprising the step of removing or disrupting at least a portion of an epithelial layer on the cornea of the eye.

* * * * *